(12) United States Patent
Rundfeldt et al.

(10) Patent No.: US 6,472,165 B1
(45) Date of Patent: *Oct. 29, 2002

(54) MODULATORY BINDING SITE IN POTASSIUM CHANNELS FOR SCREENING AND FINDING NEW ACTIVE INGREDIENTS

(75) Inventors: Chris Rundfeldt, Coswig (DE); Rainer Netzer, Hamburg (DE)

(73) Assignee: Arzneimittelwerk Dresden GmbH, Radebeul (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/368,314

(22) Filed: Aug. 3, 1999

(51) Int. Cl.[7] ............... C12Q 1/02; C12Q 1/68; C12Q 1/00; C12N 5/00
(52) U.S. Cl. ............... 435/29; 435/4; 435/6; 435/7.2; 435/7.8; 435/375; 530/350
(58) Field of Search ............... 435/29, 7.8, 375, 435/4, 6, 7.2; 530/350

(56) References Cited

U.S. PATENT DOCUMENTS 5,852,053 A * 12/1998 Rostock et al. ............ 514/485

FOREIGN PATENT DOCUMENTS

| WO | PCT US98/13276 | 8/1997 |
| WO | PCT GB98/03720 | 12/1997 |
| WO | PCT US98/22375 | 10/1998 |
| WO | WO 01/01970 A2 | 1/2001 |

OTHER PUBLICATIONS

Herman J.C. Berendson, Science 282:642–643, 1998.*
Rundfeldt, C., European Journal of Pharmacology, 336:243–249, 1997.*
Rostock, A. et al. Epilepsy Research 23:211–223, 1996.*
Rundfeldt et al., Neuroscience Letters, 282, 73–76 (2000).
Rundfeldt, Epilepsy Research, 35, 99–107 (1999).
Main et al., Molecular Pharmacology, 58, 253–262 (2000).
Wickenden et al., Molecular Pharmacology, 58, 591–600 (2000).
Schroeder et al., Nature, 396, 687–690 (1998).
Wang et al., Science, 282, 1890–1893 (1998).

* cited by examiner

Primary Examiner—David Guzo
Assistant Examiner—Gerald G. Leffers, Jr.
(74) Attorney, Agent, or Firm—Fulbright & Jaworski L.L.P.

(57) ABSTRACT

A selective modulatory retigabine binding potassium channel receptor site containing subunits KCNQ2 and KCNQ3, and a method for directly selectively modulating that receptor site by administering retigabine to a cell preparation of the potassium channel.

11 Claims, No Drawings

MODULATORY BINDING SITE IN POTASSIUM CHANNELS FOR SCREENING AND FINDING NEW ACTIVE INGREDIENTS

FIELD OF INVENTION

The invention relates to a new, selective modulatory binding site in potassium channels for screening and finding new active ingredients for the treatment of diseases, which can be attributed to a hyper excitation or a deficient excitability of neuronal cells.

BACKGROUND

Potassium channels have various definite functions in excitable cells, and not excitable cells. These functions include, for instance, the control of the membrane potential, the regulation of insulin secretion from pancreatic β-cells, the control or the release of cytokines from T lymphocytes, the regulation of the salt and water equilibrium in kidney cells, and the control of the electrical excitability and synaptic plasticity of neurons. It is therefore not surprising that the activity of the potassium channels is subject to a plurality of control mechanisms, which include the redox potential of a cell, the secondary messenger systems, namely calcium and cyclo-adenosine monophosphate (c-AMP), protein kinases and phosphatases, and the membrane potential. Moreover, the structures of previously characterized potassium channel proteins have numerous variations of different basic motifs and are thus very heterogeneous. On the basis of these various functions, it is also not surprising that different potassium channels occur ubiquitously in the plant and animal kingdoms (Sewing, S., Röper, J., and Pongs, O.: Structure and function of voltage-gated $K^+$ channels. Euroforum 2, 21–28, 1996).

Potassium channels selectively fulfill their heterogeneous tasks due to these manifold structures and in conjunction with the very large band width of the modulation paths. Substances, which selectively modulate the potassium channels are interesting medicinal drugs for a plurality of different diseases. Potassium channels are discussed in the literature as targets for the treatment of strokes, epilepsy, Alzheimer's disease, psychiatric diseases, sleep disorders, cardiac arrhythmiasis, diabetes type II, osmotic dysfunctions such as in the case of glaucoma, tumor cell growth, but also for inflammation processes and for learning disorders, for high blood pressure, incontinence and asthma.

It was previously possible to successfully implement the treatment of diabetes, of cardiac arrhythmiasis and of high blood pressure with selective medicinal drugs (Sewing et al., see above).

In 1998, Schröder et al. reported for the first time that a mutation-induced, slight interference with only one member of the large family of potassium channels can substantially interfere with the fragile equilibrium between excitation and inhibition of excitable cells. In the case of this particular channel, it is a heterooligomer consisting of the subunits with the names of KCNQ2 and KCNQ3. The function of this channel is reduced by about 25% through mutation of one of the two subunits. This causes affected patients to suffer epileptic attacks already in early infancy (Schröder, B. C., Kubisch, C., Stein, V., Jentsch, T. J., Moderate loss of function of cyclic-AMP modulated KCNQ2/KCNQ3 $K^+$ channels causes epilepsy. Nature 396, 687–690, 1998). This channel is the first potassium channel, to which a human disease can be unambiguously assigned. Schröder postulates that a positive modulation of this channel should produce a strong anticonvulsive effect. He concludes that, by increasing the level of the intracellular seconal messenger cAMP, the activity of the channel can be positively affected; in his in vitro systems, he was able to show that the activity of the channel actually increases as the cAMP level increases.

At about the same time, Wang et al. (Wang, H. S., Pan, Z., Shi, W., Brown, B. S., Wymore, R. S., Cohen, U. S., Dixon, J. E., McKinnon, D., KCNQ2 and KCNQ3 potassium channel subunits: molecular correlates of the M-channel. Science 282, 1890–1893, 1998) showed that the above-mentioned heterooligomeric channel, confirmed in man and consist of KCNQ2 and KCNQ3, is the molecular correlate of the M channel, the functions of which were described long ago.

The M channel is formed selectively only in neuronal cells (see Schröder et al., and Wang et al., above) and is coupled there over intracellular signal proteins (G proteins) selectively in the central nervous system to muscarinergic sub-types of the acetylcholine receptor. The channel is not expressed in the peripheral tissue. The activity of the channel is lowered by muscarine agonists and raised by muscarine antagonists.

The muscarine agonist, pilocarpin, initiates severe convulsions in animals. The resulting destruction of the cells, in which the muscarine receptor (and also of the M channel) is expressed, causes the animal to develop spontaneous epileptic episodes after this treatment.

By means of a different muscarine agonist, oxotremorin, an essential tremor, which simulates the tremor of Parkinson's patients, can be initiated in the animal by sub-lethal doses. Muscarine-antagonistic substances are used clinically for the treatment of this tremor.

From these presentations, which are given by way of example, it becomes clear that an indirect modulation of the M channel (initiated over muscarine receptors or caused by an increase in the cAMP level) represents a highly interesting possibility for intervening in different diseases.

In particular, this is to be shown in greater detail for several diseases.

Epilepsy

Epilepsy is characterized by the repeated occurrence of convulsions. It occurs at the rate of 0.5 to 1% of the population. Epileptic convulsions result from an abnormal synchronization and a massive discharge of a large number of nerve cells in a nerve cell association in the brain. Depending on the participation of different regions of the brain, this results in a paroxysmal temporary disturbance in motor activity (motor convulsions), emotional state, behavior or perception (Janz, D. (1985) Epilepsy: Seizures and syndromes. In: Frey, H. H. and Janz, D. eds., Antiepileptic drugs. Handbook of experimental pharmacology, Vol. 74, pp. 3–34, Springer-Verlag, Berlin, Heidelberg, New York, Tokyo); (Porter, R. J., Classification of epileptic seizures and epileptic syndromes. In: Laidlaw J., Richens A., Chadwick D., (eds.): A Textbook of Epilepsy. Churchill Livingstone, N.Y., 1993, pp. 1–22).

However, the convulsion is only one symptom, which principally can be initiated in each individual, when the stimulus for activation and synchronization is sufficiently strong. Epilepsy is therefore characterized by an increased sensitivity to external or internal stimuli for synchronization and activation. The excitability and the sensitivity of the nerve cells is greater in epileptic patients.

As mentioned above, it was possible recently to show that potassium channels, which are composed of the subunits KCNQ2 and KCNQ3, have a decisive controlling effect on the excitability of nerve cells (Schröder et al., supra). A reduction in function of these channels by about 25% already leads to epileptic attacks in infants, who do not have adequate compensatory mechanisms at their disposal. Such a weak reduction in the function of this potassium channel was detected for a genetically determined form of epilepsy, the BFNC (benign familial neonatal convulsions) variety (Schröder et al., supra). This potassium channel can be detected only in the brain and in nerve cells, but not in other tissue (see Schröder et al., supra; and Wang et al., supra).

It has not yet been possible to clarify the genetic cause for other forms of epilepsy. However, the disease is always associated with an increased excitability of nerve cell networks. The current therapy tended to reduce the symptoms of the diseases. Established antiepileptic drugs, such as carbamazepine, phenytoin and lamotrigine act as use-dependent blockers of sodium channels. These channels are necessary in order to conduct cellular excitations along nerve fibers.

Sodium channel blockers reduce the conductance of excitations and in this way have an anticonvulsive action. The underlying hyper-excitation is however not reduced. Other antiepileptic drugs, such as phenobarbital, clonazepam, vigabatrin, topiramate or valproate intensify the inhibitory neurotransmission or reduce the excitory neurotransmission as they reduce the probability that an excitation will be transferred to other nerve cells. Here also, the cause of the disease, the underlying hyper-excitability of the individual nerve cells, is not affected; only the conduction of signals is reduced. However, medicinal drugs, which selectively positively modulate the above mentioned potassium channel can affect the excitability of the nerve cells directly. Since the channel can be detected only in neuronal tissue, a selective effect without side effects on other tissues is to be expected for such substances.

Alzheimer's Disease

As already mentioned, the potassium channel, consisting of the subunits KCNQ2 and KCNQ3, represents the molecular correlate of the M channel (see Wang et al., supra). The M channel is negatively coupled over a tight coupling to a sub-type of the acetylcholine receptor, the muscarine receptor of the central nervous system. Muscarine receptors, outside of the nervous system, are not coupled with the M channel. An activation of muscarine receptors leads to a reduction in the probability that this channel is open and thus to a reduction in the function.

This is already used pharmacology. Due to a weak inhibition of acetylcholine esterase, an enzyme that decomposes acetylcholine, by means of medicinal drugs, such as Donepezil-HCl (such as is sold under the trademark Aricept®), the acetylcholine concentration in the brain is increased and the muscarine receptor activated, as a result of which the potassium channel is negatively modulated (inhibited). This results in an increase in the excitability of cholinergic nerve cells. In Alzheimer's disease, cholinergic nerve cells are selectively destroyed, which leads to the known symptoms of loss of memory (dementia). By increasing the excitability of the remaining cholinergic nerve cells, the latter can compensate for the functions of the destroyed nerve cells, as a result of which the loss of memory is counteracted.

However, the enzyme inhibitors of the cholinesterase have decisive disadvantages. Since cholinergic signal transduction plays an important role in the whole of the body and thus also in the skeletal muscles and in other tissues, and since the substances inhibit cholinesterase everywhere, there is a plurality of side effects, such as dizziness, dyspepsia, abdominal pain, nausea and/or vomiting, diarrhea, anorexia and myalgia. Occasionally, weakness, ataxia, sleeplessness, weight loss and bradycardia also occur.

The substance, linopirdine, is in development to avoid these disadvantages. It does not affect the cholinergic system. Instead, it blocks the M channel (=KCNQ2+KCNQ3) (see Wang et al., supra). However, this medicinal drug has the disadvantage that it does not have a sufficient selectivity for the M channel. Channels with a similar affinity, which play a major role in the function of the heart muscle, are blocked. These channels are, in particular, the KCNQ1 channel, but also the eag1, erg1, erg3, elk1, Kv1.2 and Kv4.3 channels, which are widespread in the heart and in other tissue (see Wang et al., supra).

The objective of selectively inhibiting KCNQ2/3 could therefore not be achieved with medicinal drugs, which modulate the linopirdine binding site. The new ligand for the linopirdine binding site, XE991, inhibits the KCNQ1 and Kv4.3 channels with a similar affinity. These two channels are important for the functioning of the heart. A blockade of these heart-specific channels can initiate fatal arrhythmias, so that a further development of this substance is questionable.

Parkinson's Disease

A modulation of central muscarine receptors is an aim also for the treatment of other diseases. For example, muscarine receptor antagonists are used for Parkinson's disease to treat the symptoms, above all, the tremor. However, as with Alzheimer's disease, the selectivity of muscarine receptor ligands for central receptors is inadequate also here, and there are undesirable side effects due to interactions with peripheral muscarine receptors and other ion channels and receptors. Since central muscarine receptors are coupled with the M channel, this function can be exercised more selectively by M channel activators than by muscarine antagonists. However, these medicinal drugs have not yet been described previously.

Neurodegenerative Diseases

Aside from the diseases mentioned above, affecting the excitability of nerve cells also plays an important role in neurodegenerative diseases (Rundfeldt, C., Potassium channels and neurodegenerative diseases. Drug News and Perspectives 12, 99–104, 1999).

Nerve cell degeneration occurs whenever there is an imbalance between energy consumption and energy supply. For example, in the case of a stroke blood is not supplied and nerve cells die. In the case of toxic hyper-excitations, as in the case of the epileptic state or amyotrophic lateral sclerosis, the cells increasingly consume energy due to hyper-excitation, and the supply of new energy is no longer adequate (see Rundfeldt et al., supra). In addition, the neurotransmitter, glutamate, is secreted by the cells. Because of the increased concentration of glutamate and the inadequate energy supply, the neurons can no longer maintain the membrane potential and depolarize. As a result of the activation of the KCNQ2/3 channel, the cells are hyperpolarized and can recover from the described noxae.

A selective lowering of the excitability of such nerve cells can therefore prevent nerve cell destruction. However, aside from lowering the temperature of the body, there was no reliable direct method of lowering the excitability of nerve cells until now (see Rundfeldt et al., supra).

Through the discovery of the significance of the KCNQ2/KCNQ3 channel for the selective control of the excitability of nerve cells, it became evident that an activation of this channel can prevent nerve cell damage. For the reasons indicated, it is necessary selectively to affect the channel with the subunits KCNQ2 and KCNQ3, to achieve a selective, for example, anticonvulsive, anti-Parkinson and neuroprotective effect upon activation and a selective memory-enhancing effect upon inhibition. Aside from the mentioned diseases, all states can be affected which are associated with a hyper-excitation or a lack of excitation of nerve cells which carry the M channel or lie in its projection fields.

This objective cannot be achieved with previously available medicinal drugs and treatment strategies.

DESCRIPTION OF THE INVENTION

Pursuant to the present invention, it was now possible to show that the anticonvulsive drug, retigabine (see Rundfeldt, supra, and Rostock, A., Tober, C., Rundfeldt, C., Bartsch, R., Engel, J., Polymeropoulos, E. E., Kutscher, B., Löscher, W., Honack, D., White, H. S., and Wolf, H. H. D-23129: a new anticonvulsant with a broad spectrum activity in animal models of epileptic seizures. Epilepsy. Res. 23, 211–223, 1996), highly selectively activates, that is, positively modulates the channel consisting of the subunits KCNQ2 and KCNQ3. Retigabine has the following formula:

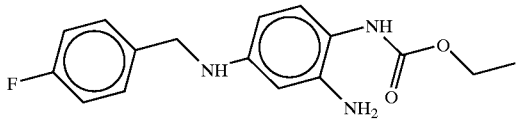

Until now, a direct positive modulation of this potassium channel was not possible. No modulatory binding sites were known, which can be engaged by substances to modulate the channel positively or negatively. Substances, such as linopirdine and XE991 (see Wang et al., supra), were only able to block the channel. These substances, moreover, are not adequately selective, so that they probably also affect the region of the channel pore, a region, which is similar in all potassium channels and is responsible for the selectivity of the channel for potassium ions. Substances, which affect the level of the messenger material, cAMP, or substances, which affect the muscarine receptor, exert only an indirect, non-selective effect on the channel.

The anticonvulsive action of retigabine can be attributed to the potassium channel activation (Rundfeldt, C., The new anticonvulsant retigabine (D-23129) acts as an opener of $K^+$ channels in neuronal cells, Eur. J. Pharmacol., 336 (1997) 243–249; Rundfeldt, C., Characterization of the $K^+$ channel opening effect of the anticonvulsant retigabine in PC12 cells. Epilepsy Res. 35, 99–107, 1999b).

Retigabine, a 2-amino-4-(4-fluorobenzylamino)-1-ethoxycarbonyl-aminobenzene and a method for its synthesis were described for the first time in European patent No. 554,543.

Investigations have shown that retigabine has no effect on a large number of different potassium channels (see Table 1). These are, in particular: Kir1.1 (ROMK1), Kir2.1 (IRK1), Kir2.2 (IRK2), Kir2.3 (IRK3), Kir3.1 (GIRK1), Kir3.2 (GIRK2), Kir3.3 (GIRK3), Kir3.4 (GIRK4), TWIK1, heteromultimeric channels of GIRK1 and GIRK2, of GIRK2 and GIRK4, of GIRK2 and GIRK3, r-eag1, r-erg1, r-erg3 and ATP-dependent potassium channel (Kir6.2).

It was possible to characterize a binding site with retigabine, which is highly selective for the channel, consisting of the subunits KCNQ2 and KCNQ3. In addition, retigabine activates the homomultimerous channel, which contains only the subunit KCNQ2. Only marginal voltage-dependent currents are measurable in cells, which express only the homomeric channel from the KCNQ3 subunit. In these cells, a current cannot be initiated by the application of retigabine (see Table 1). Heteromultimeric channels, consisting of KCNQ2 and KCNQ3, were identified as a molecular correlate of the M channel in nerve cells. On the other hand, homomultimeric channels which contain only KCNQ2 and KCNQ3 subunits, admittedly can be produced artificially in cell culture systems but have not been detected so far in vivo. It can be assumed that the heteromultimeric channel containing KCNQ2 and KCNQ3, is the physiologically occurring form of this potassium channel and that retigabine selectively activates this channel.

This is the first proof that a selective, positive modulation of this channel is possible, that is, that the channel has a modulatory binding site, which lies outside of the channel pore. During the binding of the ligand, binding sites within the channel pore lead to a blockade of the duct. We were able to show that the binding site for retigabine lies on the channel subunit KCNQ2. Homomultimeric channels, which contain only the subunit, KCNQ2, are activated by retigabine. However, in nerve cells, only heteromultimeric channels can be detected with the KCNQ2 and KCNQ3.

The effect of retigabine on these heteromultimeric channels is very great and is concentration dependent. If the channel is affected positively to the maximum extent by the intracellular addition of saturating concentrations of the stable cAMP analog 8Br cAMP (10 $\mu$M), as described by Schröder et al., supra, a distinct activation can still be initiated by retigabine. By these means, we were able to show that the selective action of retigabine is independent of the cAMP content of the cell. Therefore, effects can be initiated by retigabine, which go beyond those described by Schröder et al., supra.

TABLE 1

The effect of retigabine on different cloned potassium channels

| Potassium Channel Subunit | Expression System | Effect of 10 $\mu$M of Retigabine |
|---|---|---|
| Kir1.1 (ROMK1) | Xenopus oocytes | No effect |
| Kir2.1 (IRK1) | Xenopus oocytes | No effect |
| Kir2.2 (IRK2) | Xenopus oocytes | No effect |
| Kir2.3 (IRK3) | Xenopus oocytes | No effect |
| Kir3.1 (GIRK1) | Xenopus oocytes | No effect |
| Kir3.2 (GIRK2) | Xenopus oocytes | No effect |
| Kir3.3 (GIRK3) | Xenopus oocytes | No effect |
| Kir3.4 (GIRK4) | Xenopus oocytes | No effect |
| TWIK1 | Xenopus oocytes | No effect |
| GIRK1 & GIRK2 | Xenopus oocytes | No effect |
| GIRK2 & GIRK4 | Xenopus oocytes | No effect |
| GIRK2 & GIRK3 | Xenopus oocytes | No effect |
| r-eag1 | CHO cells | No effect |
| r-erg1 | CHO cells | No effect |
| r-erg3 | CHO cells | No effect |
| KCNQ2 | CHO cells | Weak activation by supplying 10 $\mu$M of retigabine (165 ± 65 pA) |
| KCNQ3 | CHO cells | No effect |
| KCNQ2 & KCNQ3 | CHO cells | Very strong activation by supplying 10 $\mu$M of retigabine (1527 ± 177 pA) |
| KCNQ2 & KCNQ3, in the presence of stable cAMP analogs | CHO cells | Strong activation by supplying 10 $\mu$M of retigabine (1100–1400 pA) |

Description of the Method Relating to Table 1

For the experiments with xenopus oocytes, the experimental amounts known to be successful for transfections i.e. 500 pg to 37 ng, of hereditary information (cRNA) for the channel to be investigated, which is known from the literature, present as clone and replicated by means of a polymerase chain reaction, was applied by pressure injection into the egg cells. After this treatment, the oocytes were placed in a nutrient medium and kept alive. After one week, the egg cells were brought individually into a recording chamber and, using the two-electrode voltage clamp method, investigated electrophysiologically. For this purpose, the egg cells, starting out from a holding potential of −80 mV, were hyperpolarized and depolarized for, in each case, 2 seconds, in 10 mV steps to different membrane potentials between −130 and +30 mV and the resulting membrane current was measured. These experiments were carried out in the presence of a control solution as well as of 1, 10 and 100 $\mu$M of retigabine and the current voltage curves obtained were compared. It was not possible to affect the activity of the transfected potassium channel by retigabine in any of the preparations investigated. In the case of the experiments, carried out in CHO cells, the CDNA transfection for the channel to be investigated was also performed by means of liposomes and the recording by means of the patch clamp technique was carried out 48 to 72 hours after the transfection. Once again, the cells were kept at −80 mV and hyperpolarized and depolarized in 10 mV steps from −100 to +50 mV in the presence of a control solution or retigabine. In addition, in accordance with a method already described (Rundfeldt, 1999b), retigabine was added at a concentration of 10 $\mu$M to cells, which were slightly depolarized (−60 or −50 mV), and the current induced thereby was quantified. The latter method was employed in order to quantify the currents shown in the Table and induced by retigabine. In cells, in which it was possible to activate a current by supplying retigabine, that is, in cells, which contained the subunit KCNQ2 or KCNQ2 together with KCNQ3, the current voltage curve, obtained by stepwise hyperpolarization/depolarization, was shifted in its activation to more negative potentials. From this, it follows that the channel is open earlier and, associated therewith, that the neurons are hyperpolarized. To check whether the activation of the KCNQ2/3 channel (M channel), initiated by retigabine, is still possible when the channel, as described by Schröder et al., 1988, is activated maximally by cAMP, a saturating concentration of the nonhydrolyzable cAMP analogon, 8-bromo-cAMP, was added to the pipette solution in some experiments. Even under these saturated conditions, retigabine was able to activate the channel strongly.

By using the modulatory binding site of the present invention, it is now possible to search for new substances, which modulate the above-mentioned channel either positively (activate) or also negatively.

A prerequisite for initiating an effect is the binding of a possible active ingredient to an endogenous substance, which is referred to as receptor. A change in the conformation must be produced by the binding in this binding site. The change in conformation leads to a change in function of the receptor affected. This process brings about the actual effect of the active ingredient, which is to be tested, at the receptor. On the basis of this knowledge, different screening systems can now be built up, with which new, even more selective or stronger-acting ligands for activating or inhibiting the M channel can be found.

The simplest implementation of a screening system is a binding assay. For this purpose, a specific, isotope-labeled ("hot") ligand for the binding site to be investigated, the same ligand in an unlabeled ("cold") form as well as test substances to be investigated and a protein preparation, which contains the receptor, are required. Equipment and procedures for carrying out the binding assay are commercially available or have frequently been described. Initially, the protein fraction for saturating unspecific binding sites is mixed with the cold specific ligands in high concentration. After the protein fraction is filtered off and rinsed, the hot specific ligand, in a defined amount, and the substance to be tested, are added in different concentrations to the protein fraction. After a defined incubation period for equilibrating both substances at the binding site, the supernatant is filtered off rapidly rinsed to remove the fraction of compound not bound to the receptor. By measuring the remaining radioactivity or a different labeling of the specific ligand in the protein fraction, it can be established whether and how much of the specific ligand is displaced from the binding site by the substance to be tested.

If the amount of specific ligand in the protein fraction decreases as the concentration of the test substances increases, then it may be assumed that the test substance displaces the specific ligand competitively from its binding site as a function of concentration and thus itself is a ligand for this binding site. Labeled and unlabeled retigabine or a ligand with even better physicochemical properties, which is characterized by retigabine, functions as hot and cold ligands. The specificity of binding assays is characterized almost exclusively by the ligand used; binding assays cannot be carried out without specific ligands. The protein preparation can have various sources. However, it must always contain the receptor that is to be investigated, in this case the M channel or the parts of the M channel, which carry the binding site, such as the subunit KCNQ2 or parts thereof.

It is of decisive importance that a competitive binding of the specific ligand at the protein is possible. The protein can be obtained from a native neuronal human tissue (postmortem or from surgically removed tissue) or from animals from cell cultures containing M channel, such as the differentiated cell line PC12 or NG108-15 or from human cell lines, such as the line hNT from cell cultures, which were provided by transient or stable transfection (=introduction of genetic information into the cell by means of methods known from the literature) with the genetic information for producing the channel subunit KCNQ2 alone or in combination with the subunit KCNQ3 or parts of the subunit KCNQ2 and which translate this information into a functional protein from other systems producing protein, such as yeast cell cultures, bacterial cultures, plant or virus cultures, provided that the genetic information for producing the receptor was implanted in the yeast, bacteria, plants or viruses.

Binding assays have the advantage that, by using specific ligands, only substances are found, which bind to the same binding site, to which the specific ligand also binds. The purity requirements, which the protein fraction must meet, are therefore not high and native material, such as brain tissue, can therefore be used for the assay. At the same time, however, the informative value of binding assays is limited. For example, it is possible to find out only if the substance to be investigated binds to the binding site in question (=receptor).

On the other hand, whether the substance, by bonding to the receptor, also initiates an action, is not investigated. Theoretically, substances are always conceivable, which bind and do not initiate an action (=neutral ligands), substances, which activate (=agonists) the substrate (here the M channel) over the receptor, or substances, which inhibit the substrate (=antagonists) over the receptor.

As mentioned above, M channel agonists are of interest, for example, for epilepsy. On the other hand, M channel antagonists are of importance, for example, for Alzheimer's diseases. It is therefore necessary to use functional tests for characterizing the action of the test substance.

The most reliable method for characterizing receptor ligands is the electrophysiological investigation on cell lines or cell cultures, similar to those described for retigabine (8). These investigations are very expensive, since each individual cell must be recorded by electrophysiological methods under visual control by means of glass electrodes. Test substance and reference substance (retigabine) are added to the cells by special application systems and the effect on the cell function is evaluated as a function of the concentration of the test substance applied.

Recently, however, more and more functional screening tests with a high throughput of substances (up to several thousand per hour, High Throughput Screening, HTS) have been described. In contrast to the binding assay, the cell function is evaluated here in comparison to the action of the specific ligand (in this case, retigabine or a ligand with even better physical and chemical properties, which has been characterized by retigabine). It is therefore necessary that the binding site, which is to be investigated, is present in a genetically defined form and, at the same time, as a functional unit in the system. The system can be cell cultures or artificially produced cell-like constructs (lipid double membranes) with a functionally embedded receptor/channel. The cell cultures must reliably and reproducibly express the receptor that is to be investigated (here, the M channel) and incorporate it functionally in the membrane.

Furthermore, a reporter system, which indicates an activation or inactivation of the channel reliably and can be read by machine, must be brought into the cells or the cell-like constructs. In order to exclude false positive results as far as possible, the cell culture, aside from the receptor, which occurs naturally or is introduced by transfection, must contain very few if any additional channels or receptors with a similar function or with a close relationship to the channel/receptor that is to be investigated.

Not only neuronal cell lines, such as the widely spread CHO cells or HEK cells, can be used as cell cultures, but also a large number of other cell lines, such as insect cell lines or human cell lines, if these have been provided by transfection with the genome for the M channel (KCNQ2/3) or also exclusively with the subunit KCNQ2 and express these functionally.

Native cell lines, which carry the M channel, such as the PC12 cell line (after differentiation with the growth factor NGF) or the NG108-15 cell line (after differentiation to the neuronal phenotype) can also be used. However, they carry the risk that, aside from the M channel, other potassium channels with similar characteristics are also expressed.

Externally added, calcium-sensitive fluorescing dyes, for example, are suitable as reporter systems. So that these dyes may be used as an indirect method for detecting a depolarization, the cell systems, aside from the potassium channels to be investigated, must also contain voltage-dependent activatable calcium channels. Since calcium channels are activated by the depolarization of cells (for example, by the blockade of the M channel) and, as a result, calcium flows into the cells, known dyes can be used, which reflect the intracellular calcium concentration. Chemiluminescence genes can also be introduced by transfection into the cell lines, which are to be used. The resulting proteins react with chemiluminescence to the calcium flowing in. M channel agonists can be detected owing to the fact that the membrane is hyperpolarized or that an externally induced depolarization is prevented. Calcium-dependent dyes indicate that, because of the absence of depolarization, there is no calcium inflow in comparison to the control.

M channel antagonists themselves initiate a measurable depolarization and lead to a calcium inflow. By these means, agonists as well as antagonists of the M channel can be found in such a system. For quantifying the effect, it is necessary to use a known standard as a positive control.

Retigabine is the first known selective M channel agonist.

What is claimed is:

1. A method for identifying a compound which positively or negatively modulates a potassium channel comprising KCNQ2 or KCNQ2 and KCNQ3 subunits, the method comprising
   (a) providing a cell culture containing the genetic information for producing the KCNQ2 subunit alone, or in combination with the subunit KCNQ3, and translating the information into a functional protein;
   (b) adding to said protein (i) a substance to be tested; and (ii) a reporter system indicating an activation or inactivation of the channel; and
   (c) observing the effect of the substance to be tested in comparison to addition of retigabine to said protein and reporter system.

2. The method of claim 1, wherein said cell culture comprises cells expressing KCNQ2 or KCNQ2 and KCNQ3 subunits.

3. The method of claim 1, wherein said cell culture comprises PC-12 or NG108-15 cells.

4. The method of claim 1, wherein said cell culture is a cell line transfected with nucleic acid encoding the KCNQ2 or the KCNQ2 and the KCNQ3 subunit.

5. The method of claim 1, wherein said reporter system is a calcium sensitive fluorescent dye.

6. A method for identifying a compound which positively or negatively modulates a potassium channel comprising KCNQ2 or KCNQ2 and KCNQ3 subunits, the method comprising
   (a) providing an artificially produced cell-like construct with a functionally embedded potassium channel containing at least KCNQ2 OR KCNQ2 and KCNQ3 subunits functionally embedded into said construct;
   (b) adding to said construct (i) a substance to be tested; and (ii) a reporter system indicating an activation or inactivation of the channel; and
   (c) observing the effect of the substance to be tested in comparison to addition of retigabine to said protein and reporter system.

7. The method of claim 2, wherein said construct is a lipid double membrane.

8. The method of claim 1, wherein said testing of said substance takes place in a high throughput screening system.

9. The method of claim 3, wherein said testing of said substance takes place in a high throughput screening system.

10. A method for identifying a compound binding to the retigabine binding site of the potassium channel comprising KCNQ2 or KCNQ2 and KCNQ3 subunits, the method comprising
   (a) providing a cell culture containing the genetic information for producing the KCNQ2 subunit alone, or in combination with the subunit KCNQ3, and translating the information into a functional protein;
   (b) adding to said protein (i) unlabeled retigabine, (ii) labeled retigabine and (iii) the substance to be tested under conditions used for a competitive binding assay, and
   (c) determining whether the substance to be tested competes with retigabine for the retigabine binding site on the potassium channel.

11. A method for identifying a compound binding to the retigabine binding site of the potassium channel comprising of KCNQ2 or KCNQ2 and KCNQ3 subunits, the method comprising (a) providing an artificially produced cell-like construct with a functionally embedded potassium channel containing at least KCNQ2 or KCNQ2 and KCNQ3 subunits functionally incorporated into said construct;

(b) adding to said protein (i) retigabine, (ii) labeled retigabine and (iii) the substance to be tested under conditions used for a competitive binding assay, and (c) determining whether the substance to be tested competes with the retigabine for the retigabine binding site on the potassium channel.

* * * * *